(12) United States Patent
Dillard (10) Patent No.: US 6,891,078 B1
(45) Date of Patent: May 10, 2005

(54) THERAPEUTIC COMPRESSIVE CUSHIONS HAVING BUCKWHEAT HULLS THEREIN

(76) Inventor: Lourdes M. Dillard, 109 Stoney Creek Dr., Florence, AL (US) 35633

( * ) Notice: Subject to any disclaimer, the term of this patent is extended or adjusted under 35 U.S.C. 154(b) by 737 days.

(21) Appl. No.: 09/661,747

(22) Filed: Sep. 14, 2000

(51) Int. Cl.[7] .................................................. A61F 5/00
(52) U.S. Cl. .............................. 602/53; 602/20; 602/23
(58) Field of Search ............................. 602/20–31, 53, 602/60–65; 606/201–202

(56) References Cited

U.S. PATENT DOCUMENTS

| | | | | |
|---|---|---|---|---|
| 3,745,998 A | * | 7/1973 | Rose ......................... 128/89 R |
| 3,901,225 A | * | 8/1975 | Sconce ....................... 128/89 R |
| 4,064,578 A | | 12/1977 | Yamada .......................... 5/355 |
| 4,657,003 A | * | 4/1987 | Wirtz ........................... 128/133 |
| 5,363,524 A | | 11/1994 | Lang .............................. 5/640 |
| 5,618,263 A | * | 4/1997 | Alivizatos ....................... 602/6 |
| 5,697,962 A | | 12/1997 | Brink et al. ................. 607/108 |
| 5,758,375 A | | 6/1998 | Horowitz ......................... 5/640 |
| 5,809,594 A | | 9/1998 | Isogai ............................ 5/645 |
| 5,916,183 A | | 6/1999 | Reid .......................... 601/134 |
| 5,976,099 A | | 11/1999 | Kellogg ......................... 602/23 |
| 6,026,330 A | * | 2/2000 | Chuang ....................... 607/100 |
| 6,058,536 A | * | 5/2000 | Henry ............................ 5/691 |

* cited by examiner

*Primary Examiner*—Nicholas D. Lucchesi
(74) *Attorney, Agent, or Firm*—J Herbert O'Toole; Nexsen Pruet, LLC (57) ABSTRACT

An device for and method of treating edema and related swelling which comprises compressive application of buckwheat hulls to a human or animal epidermal region. The device for and method of the present invention reduces interstitial swelling without requiring the removal of cool or heated packs while providing effective heat transfer. Buckwheat hulls, having this surprising heat transfer capability, additionally afford a unique compressive therapy. Moreover, buckwheat hulls are a single, inexpensive, biodegradable and non-allergenic material.

8 Claims, 11 Drawing Sheets

THERAPEUTIC COMPRESSIVE CUSHIONS HAVING BUCKWHEAT HULLS THEREIN

BACKGROUND OF THE INVENTION

1. Field of the Invention

The present invention relates generally to medical devices and methods, and in particular to a device and method for therapeutically treating edema and related swelling in a body trunk and/or extremity such as an arm, hand, foot or a leg, through compressive application of pillows containing buckwheat hulls.

2. Description of Related Art Including Information Disclosed Under 37 CFR 1.97 and 37 CFR 1.98

Edema adversely effects numerous persons and animals each year. For some, it occurs chronically, as a result either of an acquired disease or of a hereditary condition. For others edema occurs as a temporary condition, consequent to lymphatic disorders or from post-operative inflammation or stress. Swelling from edema also causes disruption of the normal flow of bodily fluids, and may cause further damage to the body.

Edema presents the problem of the presence of abnormally large amounts of fluid in the intercellular tissue spaces of the body; most commonly referring to a demonstrable accumulation of excessive fluid in the subcutaneous tissues. Edema may be localized, due to venous or lymphatic obstruction or to increased vascular permeability, or it may be systemic due to heart failure or renal disease. One type of edema characterized by the accumulation of excess fluid in the subcutaneous tissues is lymphedema.

Lymphedema may exist as the primary or secondary type. The primary type can be present from birth (congenital lymphedema) or may occur during puberty (lymphedema praecox) or less frequently later in life (lympdema tarda). Primary lymphedema occurs less often in men. The patient complains of swelling of the foot, leg, or an entire extremity. Usually unilateral, it is worse during warm weather and before menstrual periods. There are usually no visual skin changes or evidence of venous insufficiency.

Secondary lymphedema is often a result of infection, especially dermatophytosis when it occurs in the foot. The onset is explosive, with chills, high fever, toxicity, and a red, hot swollen leg. Lymphangitic streaks may be seen in the skin, and lymph nodes in the groin are usually enlarged and tender. These features distinguish it from acute thrombophlebitis. Secondary lymphedema in older persons may be due to malignant disease in the pelvis or groin. Obliteration of lymphatic tissue by excision or radiation therapy is another cause.

Secondary lymphedema frequently attends surgical procedures which are being performed with increasing frequency. Mastectomy, especially radical mastectomy and even lumpectomy involves the intentional removal of lymph nodes in the axillary region. Such removal may have a systemic effect because the injury occurs near the entrance of the lymphatic ducts to the subclavian veins. Prostatectomy, orchiectomy, bladder surgery and hysterectomy all involve significant dissection of the lymphatic system in the pelvic and abdominal areas.

The lymphatic system in the extremities parallels the venous system. In the legs, beginning in the dorsal region of the foot, the lymphatic ducts curve around the internal malleolus and ascend along the inner margin of the limb. In the arm, the system is analogous, beginning on the dorsal region of the hand and ascending to the axillary region. Trauma to any extremity, especially compound fractures, inevitably damages the lymphatic system. Finally, non-invasive diagnostic and therapeutic procedures such as radiation therapy in oncology can destroy lymph nodes or ducts in the treatment region.

Lymphedema is not only a primary concern because of the resultant swelling, heaviness and weakness causes discomfort. The diminished function of the lymphatic system predisposes the patient to opportunistic infections and further injury of a mechanical nature.

Excellent survey articles directed to the understanding and care of lymphedema include S. R. J. Thiadens, "Lymphedema, An Information Booklet", National Lymphedema Network, San Francisco, 1996, C. A. Humble, "Lymphedema", *Oncology Nursing Forum,* 22, 1503 (1995) and C. Wilson, ed., *J. Cardiovas. Nur.,* 4, 79 (1989). Treatment which is non-invasive and suffices in most cases involves massage, preferably with an external compressive device (ECD) formed from a series of chambers which inflate serially to serve as a type of peristaltic pump. Subsequently, a more portable compress may be used during "working hours." Conventional compresses are formed from some type of elastic material and, for the treatment of lymphedema and other circulatory diseases, may include shaped rubber pads. Devices of this type are heavy, breathe poorly and are generally uncomfortable in the summer. Allergic response may be a concern as many people are or become sensitized to synthetic and natural rubbers, especially latex.

An example of constant pressure devices include Schneider packs, used to compressively apply small packs of randomly placed pieces of high density foam bound within a tubular cloth pouch or tube.

U.S. Pat. No. 5,976,099 discloses compressing a plurality of particles in a multiplicity of pockets arranged in a chevron configuration against a swollen body area to thereby create a network of relatively narrow low pressure channels within a relatively large high pressure surface area. The device comprises an enclosure of compressible, high resiliency, low density, open cell plastic foam such as polyurethane particles and a compressive means with which to apply the enclosure. Though this reference suggests the simultaneous use of particles having various shapes, resiliency and density, it does not suggest the use of hollow, collapsing and expanding, hard shell particles. Nor does this reference suggest using biodegradable and naturally available particles which inherently maintain a sustained and indefinite cooling effect due to superior heat transfer properties.

U.S. Pat. No. 5,916,183 discloses a sheet of convoluted plastic foam and a means to push the extending elements, or fingers, of the convoluted foam sheet against a swollen body part. The use of solid convoluted sheets adds undue weight and restricts movement. Such device typically weighs three pounds.

U.S. Pat. No. 5,697,962 discloses a therapeutic wrap which is disposed on opposite sides of the knee and receives hot or cold substances without being removed from the knee. Even so, frequent replacement is required, which may cause pain or aggravate an associated injury.

U.S. Pat. No. 4,064,578 discloses a two layer slidable seat cushion having a fibrous layer containing buckwheat. A sponge mat layer exists between the fibrous layer and the patient. Buckwheat is used as a fibrous material to allow layer shifting. The use of granular material enables the lower portion of the patient's body to move smoothly in the forward direction without any pressure being applied to the body. Thus, this reference teaches away from the compressive therapy of the present invention.

U.S. Pat. No. 5,363,524 discloses a pillow having upper and lower fabric panels and a flowable filler material such as buckwheat hulls therebetween. This pillow provides support for the neck and other portions of the body.

U.S. Pat. No. 5,758,375 discloses a body support and bed pillow containing a granular material such as buckwheat. This pillow provides support for the neck and other portions of the body whereby users can redistribute filling material in a predetermined configuration by tightening a drawstring.

U.S. Pat. No. 5,809,594 discloses a combination pillow containing buckwheat husk which supports the cervical vertebrae and an occipital region of the user. The disclosed pillow is intended also to assist in preventing the user's head from coming off of the pillow.

U.S. Pat. No. 5,363,524 discloses a buckwheat pillow. No mention is made that such a pillow would be beneficial for the treatment of edema. More importantly, this pillow is not adapted for use in compressive therapy or for effective heat transfer.

There remains a need for a comfortable compressive device for the treatment of lymphedema which is both effective and comfortable.

BRIEF SUMMARY OF THE INVENTION

It is an object of the present invention therefore, to provide a device for and method of compressive treatment of lymphedema and other types of edema.

It is a further object of the present invention to provide a device for and method of compressive therapy for edema which is safe, comfortable and effective.

It is a further object of the present invention to provide a device for and method of compressive therapy for edema which utilizes an uniform, inexpensive, hypoallergenic material as its active component.

It is a further object of the present invention to provide a device for and method of compressive therapy for edema which applies non-uniform stimulating pressure depending on random orientation of resilient particles having either rigid or compressible characteristics depending on such orientation and movement of the body in the region of the compress.

These and other objects may be attained in the device of the present invention by providing an enclosure containing a medically effective amount of buckwheat hulls to form a pillow wherein said pillow has a surface area and shape which is adapted both for compressive application and to promote effective heat transfer. Such device thus dissipates heat from a swollen body part to buckwheat hulls contained therein.

These and other objects may also be attained in the method of the present invention by compressively applying an effective treatment amount of a plurality of buckwheat hulls contained within an elastic, breathable, fabric enclosure to reduce edema or related swelling.

DETAILED DESCRIPTION

The present invention is useful in the reduction of swelling from lymphedema and other types of edema in a simple, medically effective and cost efficient manner. The device of the present invention comprises a sleeve, shell, pocket, glove, sock or other enclosure such as a bandage wrap containing buckwheat hulls, which is adapted to be compressively applied to an epidermal region of an animal or human, and which promotes heat transfer away from the patient's epidermal region while maintaining pressure.

The method of the present invention calls for compressive application of a wrap or enclosure containing buckwheat hulls to reduce and thereby treat edema. In one embodiment, it may be directly applied to the skin under which the edema exists. Alternatively, it may be applied to the epidermal region at blood flow pressure points to achieve the effect of reducing edema in subcutaneous tissue not located at such a pressure point.

The particular and unexpected advantages of buckwheat hulls for compressive therapy for edema are multifold. First, buckwheat hulls are inexpensive. Because of their uniformity and natural availability they need no prefabrication. Secondly, buckwheat hulls are biodegradable. Thirdly, they are non-allergenic. Unlike some natural and synthetic plastics, which may cause allergic reactions, sterilized buckwheat hulls produce very few immune response reactions. Moreover, they are easily sterilized initially by ethylene oxide or steam to kill molds which normally may be found on grain and may be sterilized as needed in normal use by using a household microwave oven.

Fourthly, every buckwheat hull is both hard and resilient depending on particle orientation. Buckwheat hull size and shape affords a surprising degree of success in eliminating interstitial fluids associated with edema. Buckwheat hulls which are intact comprise three walls. Though they initially have these three walls, after time and use or, during the process of buckwheat removal, hulls may fall apart, leaving remnants of the entire hull. These remnants have either one, two or three sides of the initial hull. As such, the particular shapes in the pillows of the present invention are nonuniform even though they were at one point part of a three sided buckwheat hull. The packed hulls continue to be resilient so that pressure may be maintained over time without rewrapping.

Figure 1:
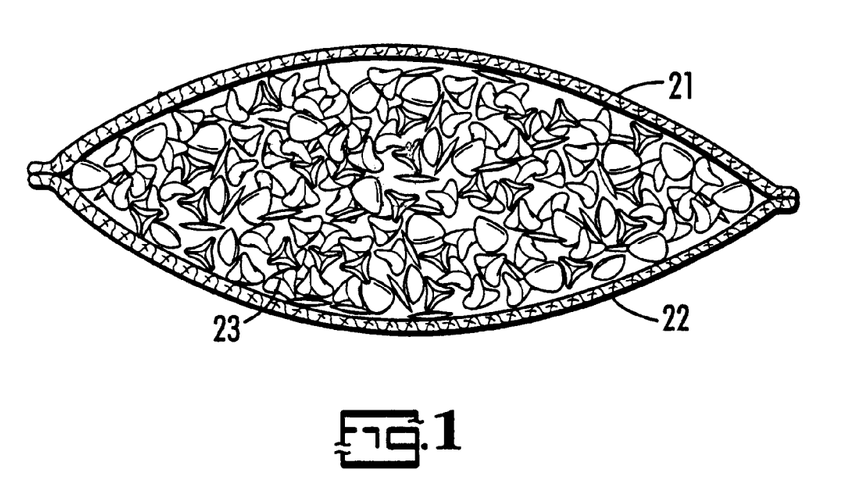
FIG. 1 is a cross sectional view of the circular buckwheat hull pillow in accordance with the present invention.

Now referring to FIG. 1, a pillow according to this invention has a first side 21 and a second side 22 encapsulating buckwheat hulls 23. The material from which the sides are made may ax be the same or different but are preferred to be "breathable."The buckwheat hull sides are extremely flat, so as to comprise a disk-like shape. Most volume within pillows according to the present invention, therefore, is occupied by air, by which heat is effectively transferred away from the patient's body. To a surprising extent, these hulls have great heat transfer properties.

This may be explained in part by the large surface area afforded by hull shape, from which thin films of vapor may evaporate. Because they afford such great number of surfaces and thus increase total surface area on which thin vapor films may collect, buckwheat hulls provide for greater rates of evaporation. At least in part through such evaporation, the buckwheat hulls promote greater heat and moisture transfer. The minimal weight is not noticed when being worn.

Figure 2:
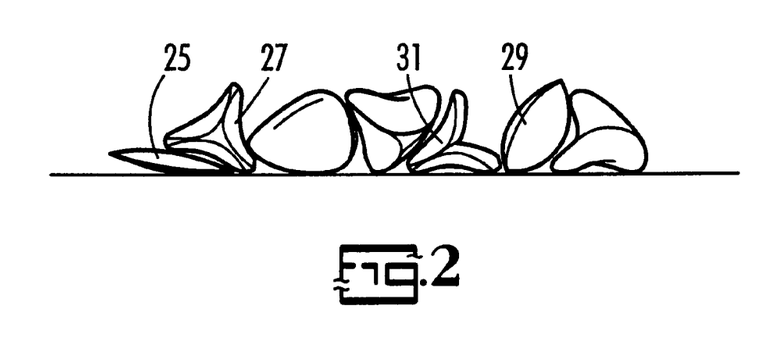
FIG. 2 illustrates several buckwheat hulls in accordance with the present invention.

Buckwheat hull particle size and shape also lend variations in the pressure applied to an affected region. As seen in FIG. 2, one sided 25, two sided 29 and three sided 31 hulls differ in compressibility and size according to their orientation with respect to the enclosure which contains them.

The present invention is not only useful for the treatment of lymphedema, but it is also useful in the reduction of a number of other types of edema found in the subcutaneous tissues. These include, but are not limited to Calabar Edema (Calabar swellings), Edema calidum (inflammatory edema), circumscribed edema (angioedema), dependent edema (edema affecting most seriously the lowermost or dependent parts of the body), edema frigidum (noninflammatory id edema), edema fugax (transient accumulation of fluid in a specific region), gaseous edema (edema accompanied with gas formation, as in gas bacillus infection and subcutaneous emphysema, giant edema (angioedema), hereditary angioneurotic edema (hereditary angioedema), inflammatory edema (a form due to inflammation, and attended with redness and pain), insulin edema (edema which sometimes follows the injection of insulin, invisible edema (the accumulation of a considerable amount of fluid in the subcutaneous tissues before it becomes demonstrable), Milton's edema (angioedema), nephrotic edema (edema occurring in nephrosis and in the intermediate stage of diffuse nephritis), non-inflammatory edema (edema without redness and pain, occurring from passive congestion or from lower serum osmolarity, non-pitting edema (edema in which the tissues cannot be pitted by pressure), periodic edema (angioedema), pitting edema (edema in which the tissues show prolonged existence of the pits produced by pressure), purulent edema (a swelling due to the effusion of a purulent fluid), Quincke's edema (angioedema), renal edema (edema due to nephritis and the consequent hypoproteinemia), rheumatismal edema (painful red edematous swellings on the limbs in rheumatism, due to subcutaneous exudation), salt edema (edema produced by an increase of sodium chloride in the diet), toxic edema (edema caused by a poison), venous edema (edema in which the effused liquid comes from the blood). Additionally, swelling caused by athletic and other injuries, including bruises, sprains and the like may be treated by the present invention.

Of these, the present invention is especially useful in the case where edema is a form consisting of subcutaneous fluid found in the limbs, hands, feet, or body torso. As such, the present invention is useful for the treatment of a number of diseases associated with the lymphatic system. These include lymphadenitis, that is, inflammation of the lymph nodes, i.e. lymph node enlargement from edema and leukocytic cellular infiltration. It also includes acute lymphangitis, i.e., acute inflammation of the subcutaneous lymphatic channels, such as usually caused by Streptococcues, pyogenes (a tumor arising from any of the cellular elements of the lymph nodes), lymphocytosis (an abnormal increase in the number of lymphocytes), lymphadenopathy (chronic swelling of lymph nodes, associated with infections). Other lymphomas susceptible to treatment using the present invention include Hodgkin's disease, Malignant Lymphomas (Non-Hodgkin's lymphoma, NHL), Burkitt's Lymphoma and Mycosis Fungoides. In many of these cases the device of the present invention is applied over the affected region.

In other cases, though, the apparatus of present invention may be applied onto the patient's epidermis not directly above the edema to be treated. For example, in another preferred embodiment, the present invention is applied over blood pressure points designated by the presence of major arterial tissue which carries blood to the subcutaneous region requiring treatment. Appropriate compressive application to these pressure points not only slows circulation to respective body parts effected by edema, but also transfers heat away from fluids flowing toward the effected region thereby decreasing the presence of excess fluid in the effected region.

For example, the present invention is useful for the treatment of lymphedema arising from breast cancer operations. Breast cancer is a serious disease in women, and a variety of modalities are employed in its treatment. Many of these treatments result in damage to the lymphatic and/or venous system which, in turn, can cause an accumulation of excessive lymph fluid and swelling of subcutaneous tissues due to the obstruction or destruction of lymph vessels. In breast cancer patients, lymphedema occurs in the arm and results in painful swelling. Excessive fluid accumulation, referred to as edema, can also arise in the arms, legs and, trunk from a variety of other causes, including infection, radiation therapy, and other conditions which result in damage to or destruction of portions of the lymphatic and/or venous system.

Whether directly applied, or indirectly at respective pressure points, the resulting reduction in edema works with an unexpected degree of success. Similar compressive treatment, and cooling application methods, when used in tandem, do not exhibit the results obtained through the method of the present invention.

Device

In a preferred embodiment, the device of the present invention comprises a medicinally effective amount of buckwheat hulls in a shaped pouch or pillow. The pillows are shaped to conform to anatomical surfaces of the body. The thickness of the pillow is normally 2 to 3 cm. when new, sufficient to compress slightly but maintain a resiliency under an appropriate wrap.

To be adapted for compressive application, the fabric enclosure is preferably made from an elastomeric fabric suitable for medicinal application to a human epidermal region. It is preferably of such resilient elasticity so as to allow stretching onto, over or around a physiological surface or body part to provide a fit sufficiently tight to compressively apply buckwheat hulls against the epidermis of the human or animal subject to treatment.

A suitable fabric will also possess a minimal water absorbency to promote effective heat transfer. The apparatus of the present invention, among other things, helps to cool either epidermal regions and subcutaneous edema lying thereunder, or epidermal regions covering arterial tissue that carries fluid to the subcutaneous edema. This is accomplished by heat transfer from the body to the pillow containing buckwheat. A major portion of the heat transfer occurs as moisture from the body is absorbed into the fabric shell, towards the buckwheat hulls, and eventually to the hulls. Warm moisture carries heat from the body to the buckwheat filling. Without such absorbency, the apparatus of the present invention may tend to act as an insulator, thereby losing its cooling feature and behaving in the same manner as rubber pads.

A suitable fabric will also possess at least some minimal degree of breathability. Porosity is determined by fiber thickness and weave. The porosity for effective breathability must exist in a stretched state. Such fabric is optionally constructed from one or more of a group of fabrics and materials to include cotton/spandex, spandex, cotton, nylon, polyester, four way stretch fabrics, easily stretching stitching, low friction fabrics, porous or breathing fabrics, absorbent cloth and other suitable materials known in the art.

Such fabric layers which comprise the pillows may be connected in various ways. The pillows may be formed by stitching, glueing or welding. To prevent lumping of the hulls, the pillow is stitched or quilted to form compartments or pockets.

The invention will be described further in terms of examples which illustrate best modes for use but are not to be considered limitations thereto.

EXAMPLE 1

Figure 3:
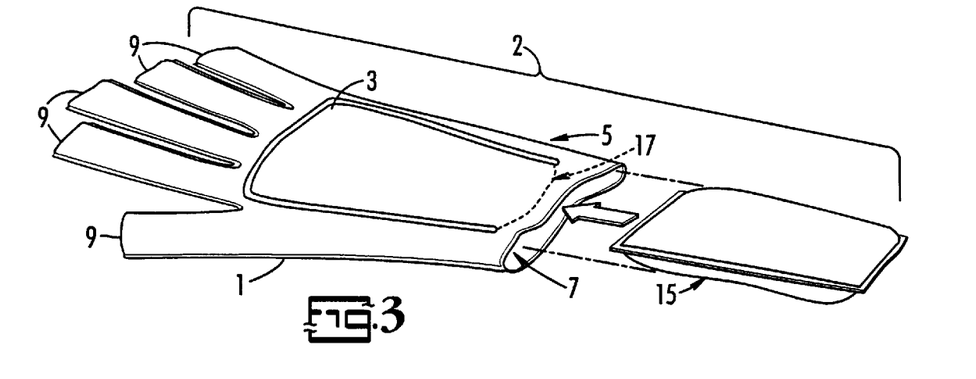
FIG. 3 is a glove having an insertable buckwheat hull pillow in accordance with the present invention.
Figure 4:
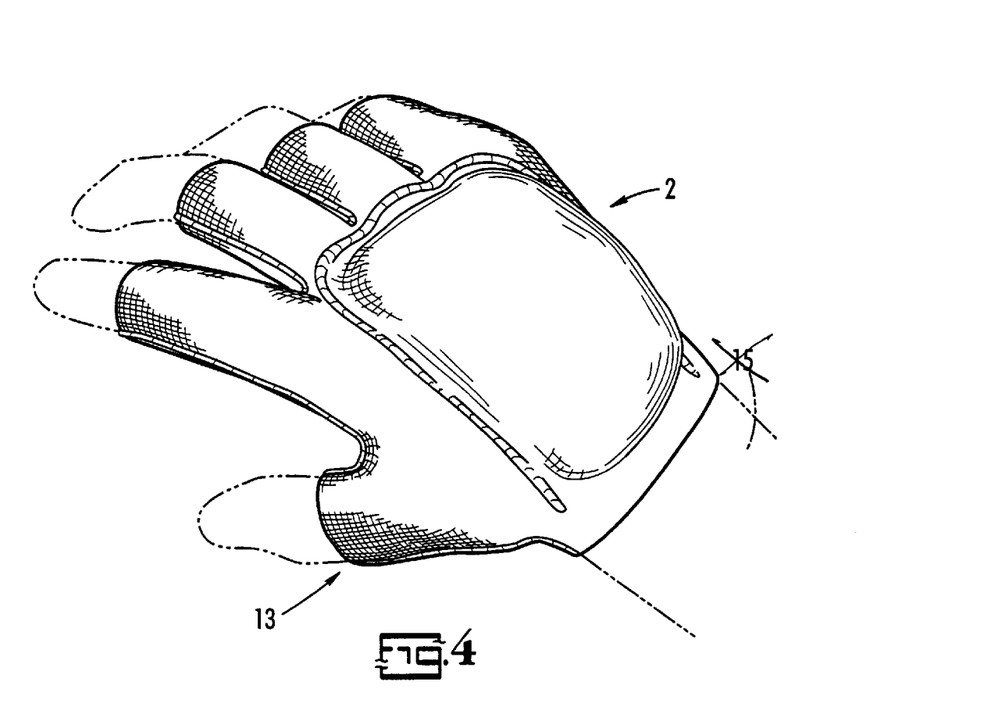
FIG. 4 illustrates compressive application of the buckwheat hull pillow in FIG. 3, in accordance with the present invention.

To reduce edema in the hands, a patient would wear a tightly fitting glove made from elastic, breathable fabric as shown in FIG. 3. Such a glove 2 contains a pocket 3 formed over the dorsal surface 5. In a typical application, the fingers are cut off 9 at the distal end to allow the wearer to sense with the finger tips. Pillow 15 stuffed with buckwheat hulls is inserted under flap 17. As shown in FIG. 4, the pillow extends from the base of the phalanges over the entirety of the metacarpal region. The elasticity of the weave of the glove 13 applies pressure to the pillow and also to the finger in this case, the buckwheat pillow either touches skin directly or through a fabric enclosure which is part of the glove.

Such a glove, in accordance with the present invention, is useful in the reduction of edema associated with, inter alia, carpal tunnel syndrome. Carpal tunnel syndrome is a clinical syndrome characterized by numbness, weakness, paresthesia or atrophy in the territory of the median nerve distal to the course through the carpal tunnel in the wrist. The transverse carpal ligament forms over the median nerve and may compress the median nerve as a result of pressure on the hand, producing the above described symptoms. Traumatic injury is exacerbated because of the narrowness of the carpal canal. There is no opportunity for the nerve to be displaced away from any compressive forces. Compressive injury can be exacerbated by the development of edema in the tissues within the canal, which because of the relatively fixed size, can cause added injury due to compression of the nerve within the canal. The glove applies pressure on the dorsal surface of the hand from the point of emergence of the lymphatic ducts across the metacarpal surface to minimize the volume of the hand and prevent stagnation of flow and the accumulation of lymph.

Referring more specifically to the glove assembly 2 in FIG. 3, the anterior or palmar 1 and the posterior or dorsal surface 3 of the flexible glove body 5 are typically sewn together in a face-to-face relationship to define the glove body 5. The material comprising the glove body 5 can include a separate glove front 1 and back 3 which are sewn together in the face-to-face relationship to define the glove body 5 or can be formed of a single piece of material which is sewn together in a sock-like fashion to define the glove body 1 having the wrist opening 7 and at least one finger opening 9.

The finger opening 9 can be partitioned or subdivided into separate finger openings by partitioning and including a line of stitching between the front side 1 and back side 3 of the glove body thereby defining separate finger openings 9 or can include the addition of a loop of material which is attached to the front side 1 and back side 3 to define the finger opening 9. Additionally, a thumb opening can be included as a finger opening 9 as shown in FIGS. 3 and 4. Again, various glove constructions can be used and made by those skilled in the art.

Now referring to FIG. 4, the flexible glove body 5 can also include a fastener or closure (not shown) located near the wrist opening 7 to secure the glove assembly 2 to the wrist portion 11 of the hand 13. The closure can include an elastic band (not shown) sewn into the flexible glove body 5 directly adjacent to the wrist opening 7 or can include a hook and looptype male/female closure as is well known to those skilled in the art. Alternatively, the glove can be a slip-on glove or other style known in the art, although it is preferable to have a fit which maintains the buckwheat hull pillow oriented.

Generally, the glove body 5 is constructed of a flexible or expandable elastic-type material which conforms to the hand 13 of the user. The flexible material provides a more secure fit for the glove assembly 2 and provides a "good feel" to the wearer of the glove assembly 2. The material which comprises the glove body 5 is preferably a stretch fabric containing cotton, nylon and spandex made by KT Medical, Inc.

EXAMPLE 2

In another preferred embodiment, the method of the present invention may be used to reduce edema, such as, for example, on a thigh or another relatively large body part.

Figure 5:
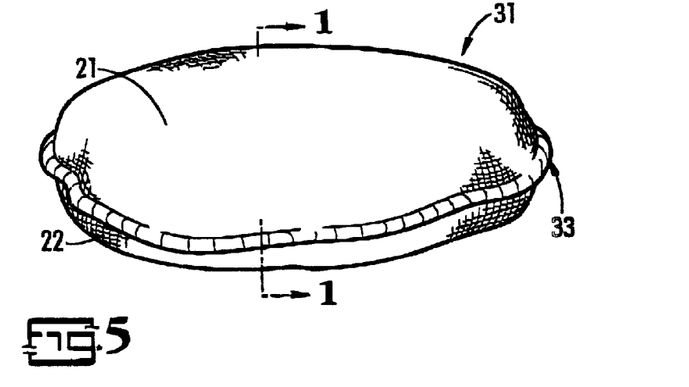
FIG. 5 is a circular buckwheat hull pillow in accordance with the present invention.
Figure 6:
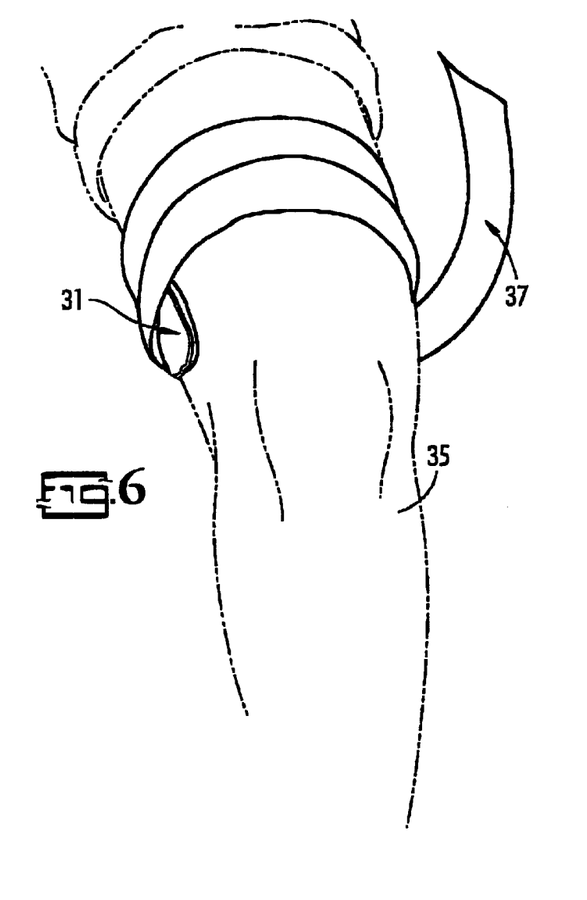
FIG. 6 illustrates compressive application of the buckwheat hull pillow shown in FIG. 5 in the region of the inner thigh.

Referring now to FIG. 5, circular pillow 31 has two sides. Side 21 is stitched to side 22 at edge 33 so as to enclose and contain buckwheat hulls. In FIG. 6 pillow 31 is compressively applied to leg 35 using a tightly wrapped bandage 37. The location shown in FIG. 6 is slightly above the inner condyle of the femur and over the inner saphenous vein. Wrap 37 may be any conventional elastic bandage wrap.

EXAMPLE 3

Figure 7:
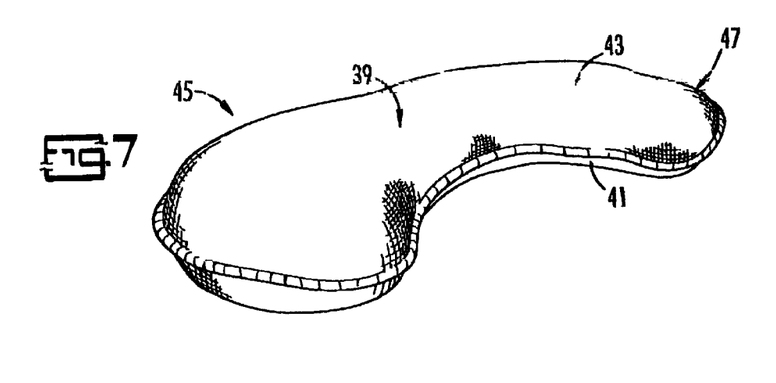
FIG. 7 is a kidney-shaped buckwheat hull pillow in accordance with this invention.

The pillow of this invention may be shaped to conform to the location of application. FIG. 7 illustrates a kidney-shaped pillow which is convenient for applications where limbs have protuberances adjacent to the area which requires compression. The pillow 45 has opposed sides 41 and 43 attached at seam 47 enclosing filler 39.

Figure 8A:
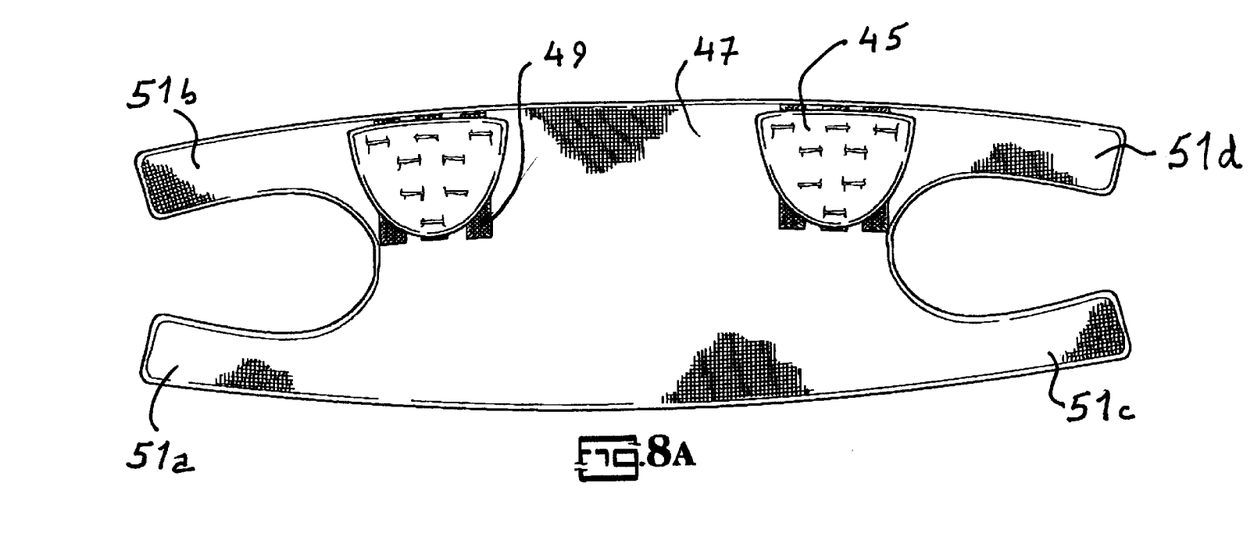
FIG. 8A illustrates compressive application of a buckwheat hull pillow in FIG. 7, in accordance with the present invention affixed to a support garment.
Figure 8B:
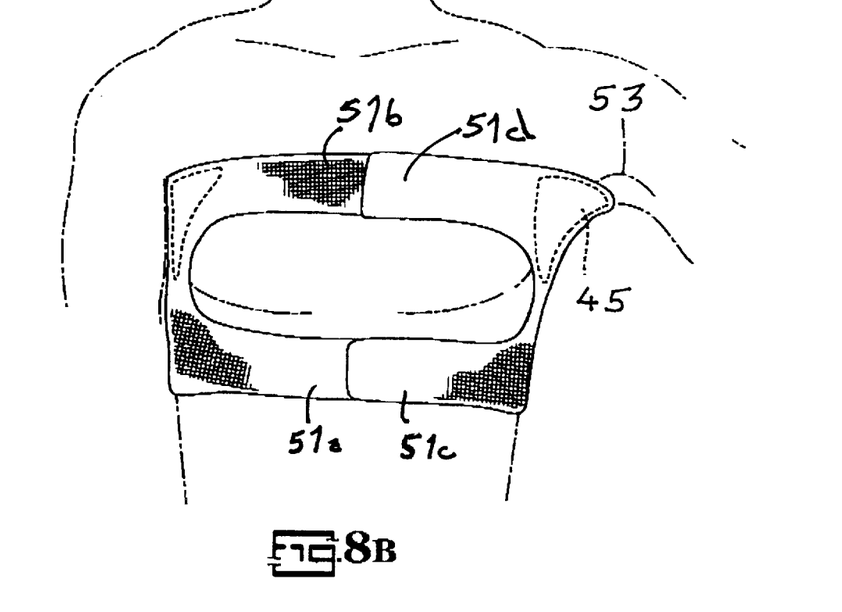
FIG. 8B illustrates the garment of FIG. 8A wrapped around the upper thorax in frontal view.
Figure 8C:
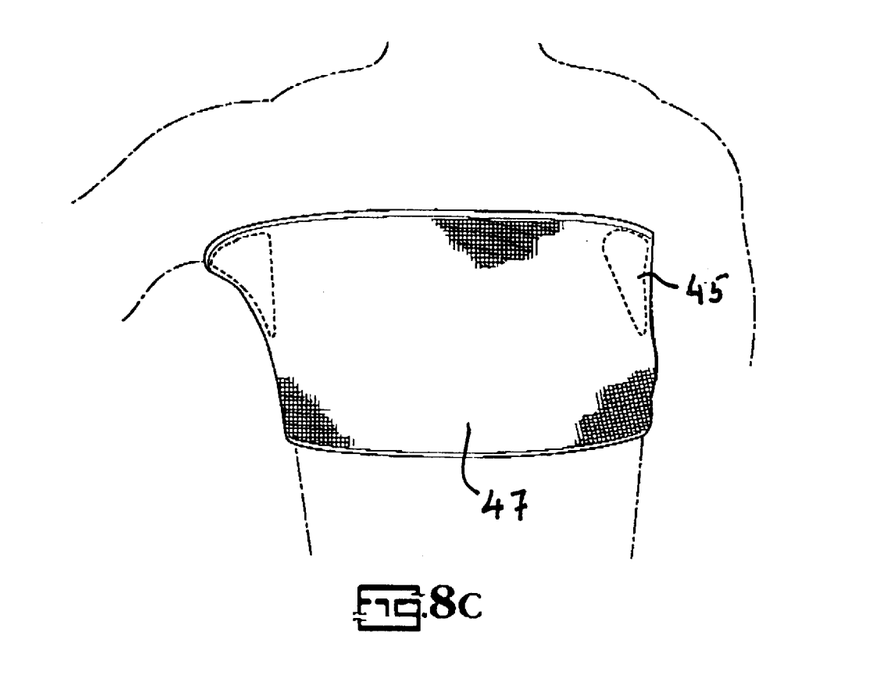
FIG. 8C is a rear view of the garment of FIG. 8B.

Pillows such as 45 may be used with a garment such as 47 and attached using hook and loop fasteners or similar means. The garment may be wrapped around a part of the body such as the upper thorax. FIG. 8A shows the opened garment with pillows attached. FIGS. 8B and 8C show the garment in anterior and posterior views for application of pillow 45 in the axillary region as would be useful for survivors of mastectomies.

EXAMPLE 4

Figure 9A:
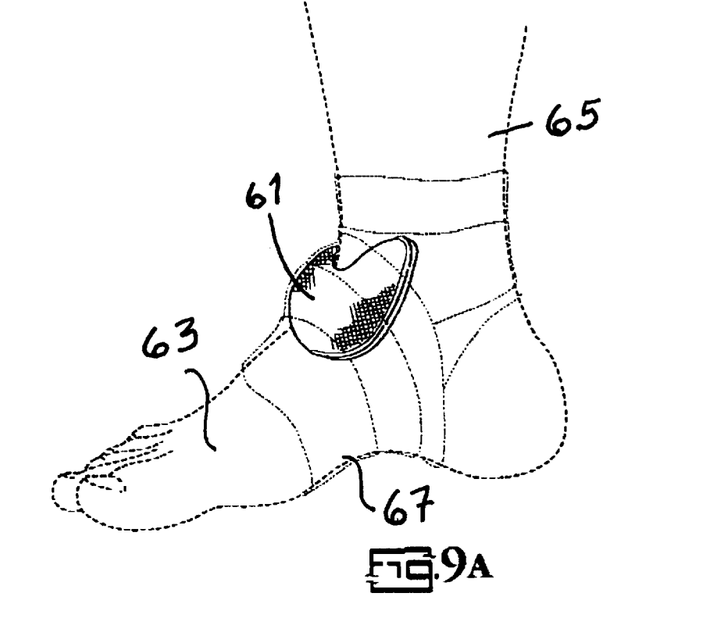
FIG. 9A illustrates the use of a kidney-shaped pillow according to FIG. 7 wrapped onto the dorsal region of a foot.
Figure 9B:
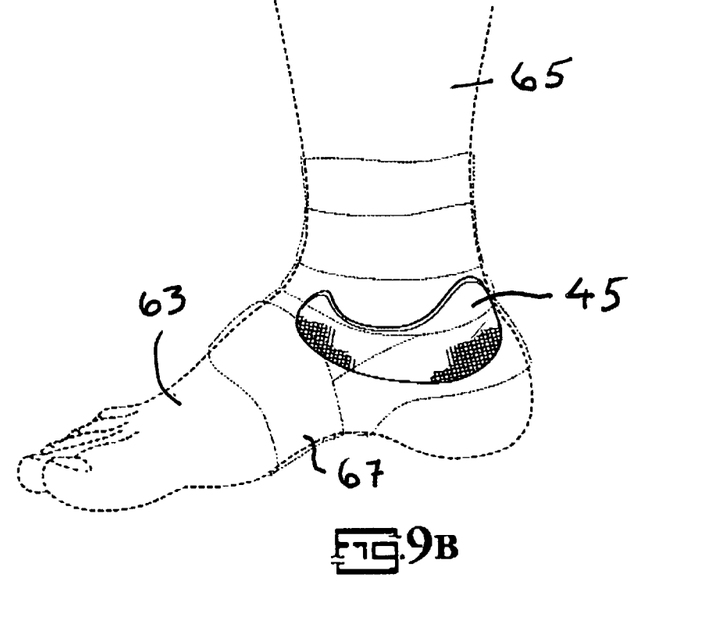
FIG. 9B illustrates the use of a kidney-shaped pillow in the malleolar region of the ankle.

The foot is a region where lymphedema is common and painful. The foot and ankle are susceptible to breakage and severe twisting and the lymphatic system of the foot is the lowest part of the body when standing. The lymphatic system begins in the dorsal area of the foot and passes around the malleolus. FIG. 9A shows a pillow 61 formed to cover part of the dorsum of the foot 63 with a wrap 67 over the foot and lower leg. The pillow may be applied to a portion of the dorsal region over the entire region from toe to ankle. FIG. 9B illustrates the use of a kidney-shaped pillow 45 on the side of the ankle, wrapped with bandage 67.

It should be noted that the wrappings shown in the figures are used to indicate the presence of a wrap. No particular wrapping pattern is intended to be shown and it is understood that manner in which the tape is run over a body part may vary by country and even by schools of training within a country.

Figure 9C:
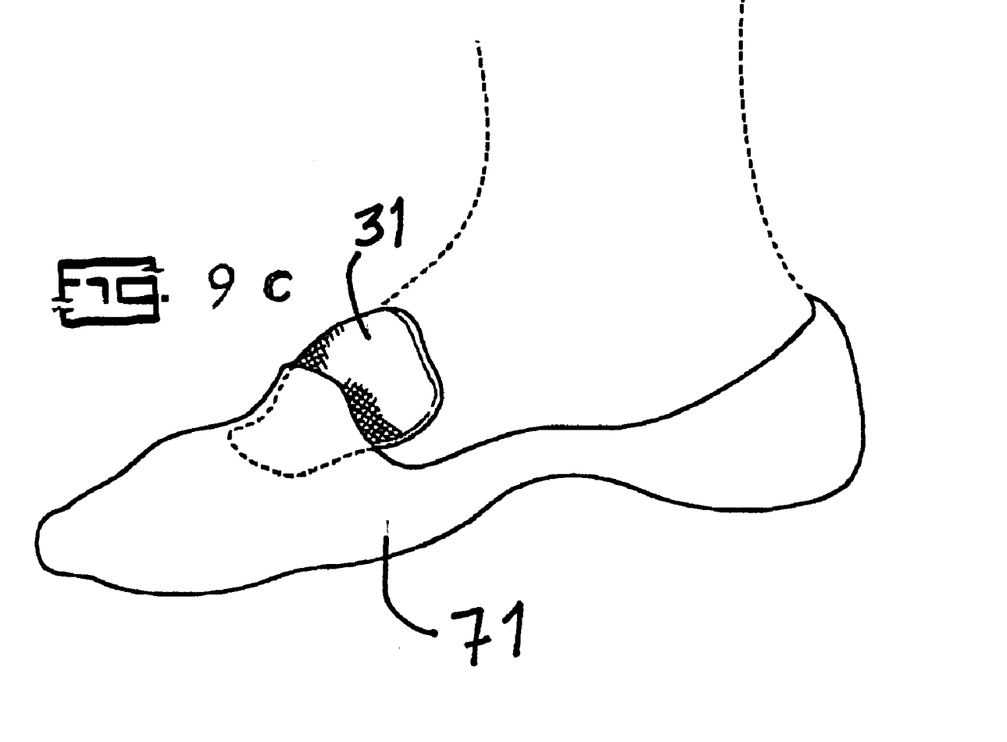
FIG. 9C illustrates the use of a buckwheat hull pillow on the dorsal region of the foot using a slipper as a wrap.

FIG. 9C illustrates an alternative method for use of a pillow which is especially convenient for elderly patients who cannot apply a wrap to their foot and ankle. The pillow 31 is held in place by a slipper or stretch sock 71 much in the manner of a glove as shown in FIG. 4.

EXAMPLE 5

Figure 10A:
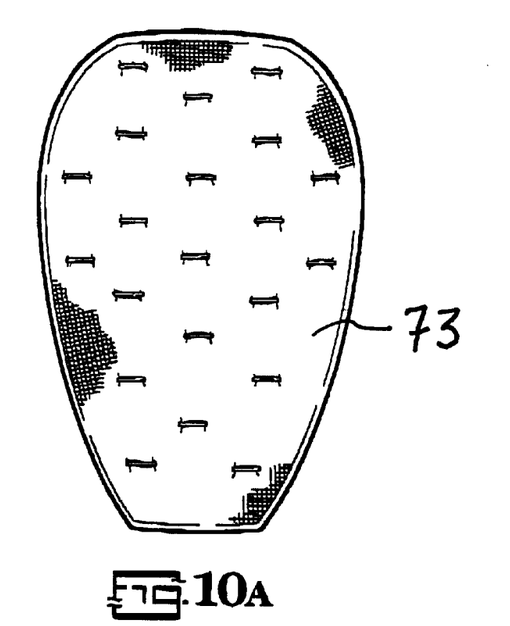
FIG. 10A illustrates an ovoid pillow according to this invention.
Figure 10B:
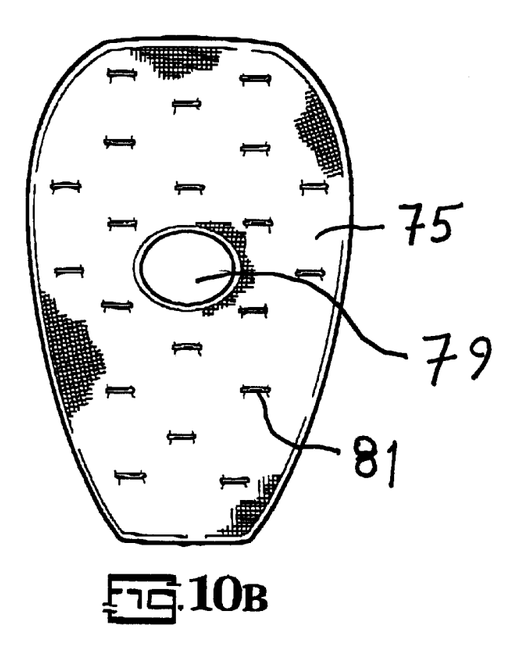
FIG. 10B illustrates an ovoid pillow according to this invention with an opening for a bony protuberance.

FIGS. 10A and 10B illustrate alternative shapes. FIG. 10A illustrates a large pad 73 which may be applied to a large part of a limb or to the torso. FIG. 10B illustrates a similar pad 75 having an opening 79 for a limb or protuberance. Stitching 81 illustrates a stitching commonly used to prevent clumping of the buckwheat hulls.

Figure 11:
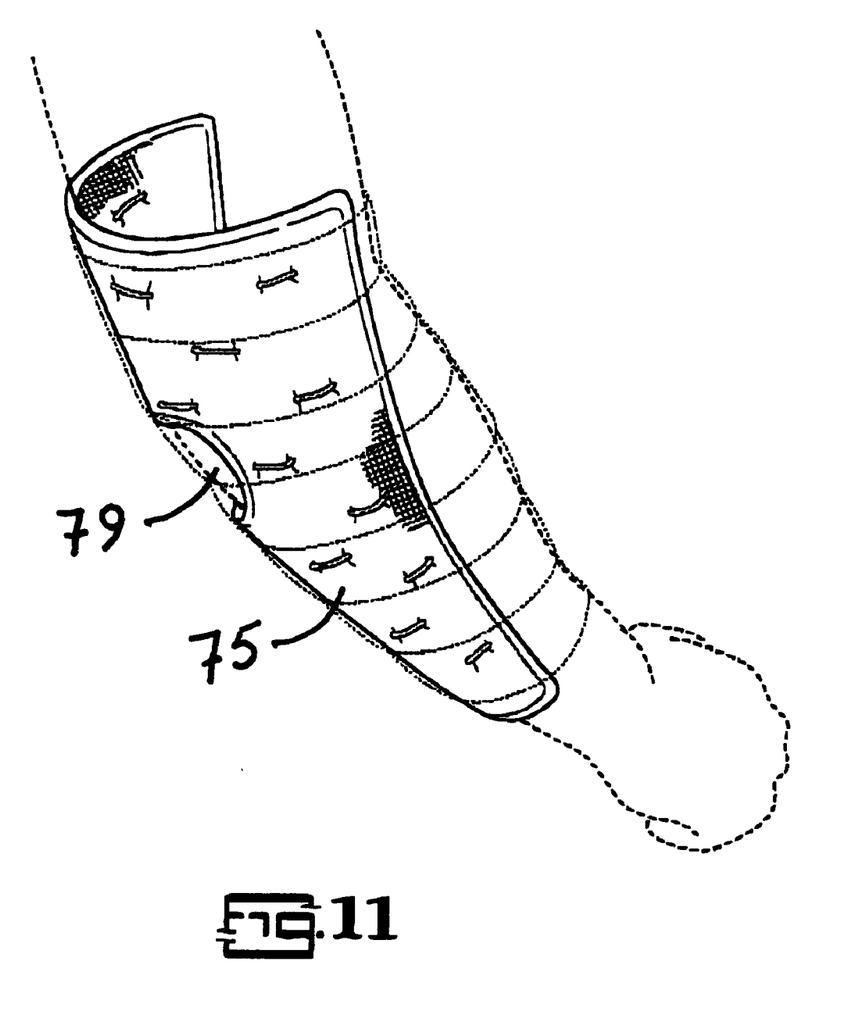
FIG. 11 illustrates the use of a pillow on a limb having a bony protuberance.

FIG. 11 illustrates the use of the pillow 75 over the lower and upper arm with hole 79 placed to allow the olecranon process of the ulna to pass through the pillow and wrap.

EXAMPLE 6

Figure 12:
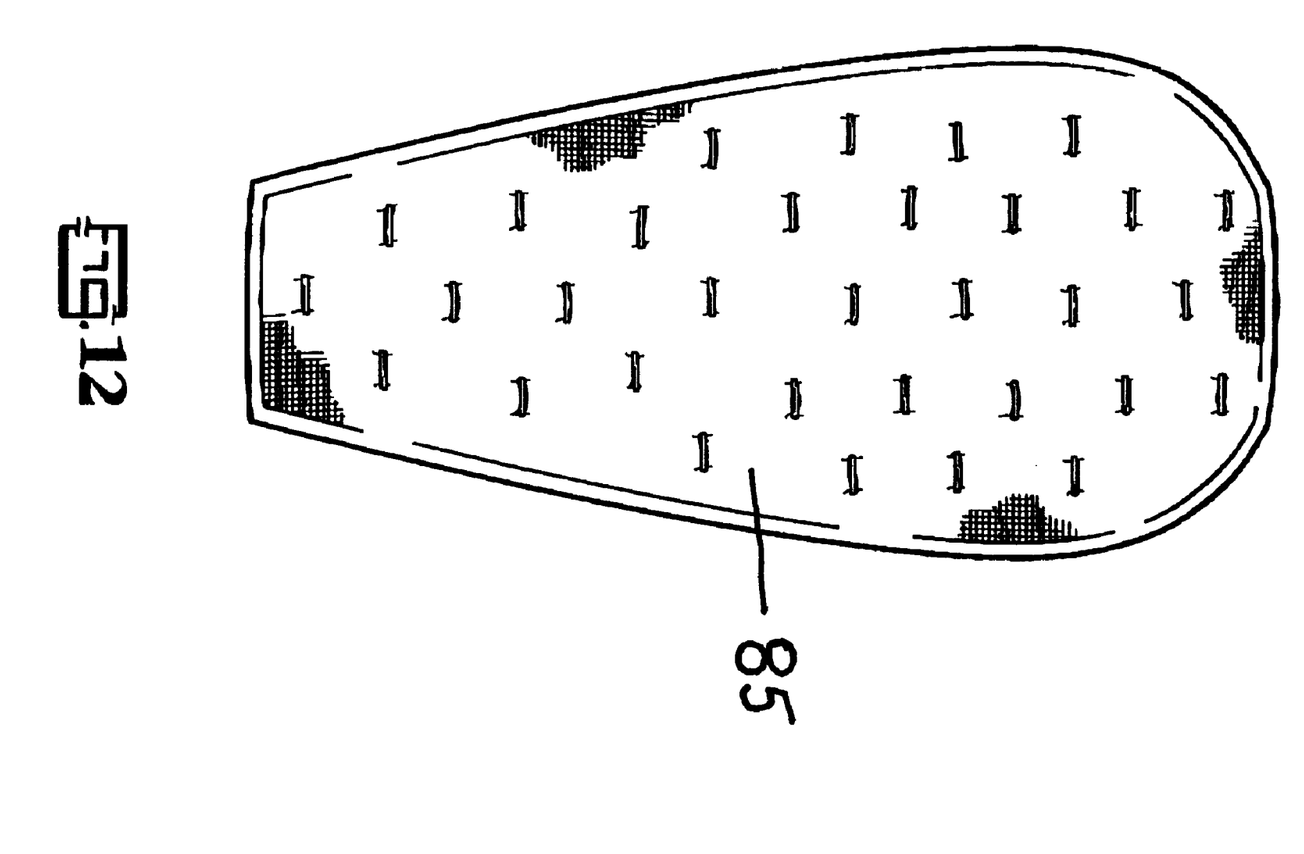
FIG. 12 illustrates an elongated pillow according to this invention.
Figure 13:
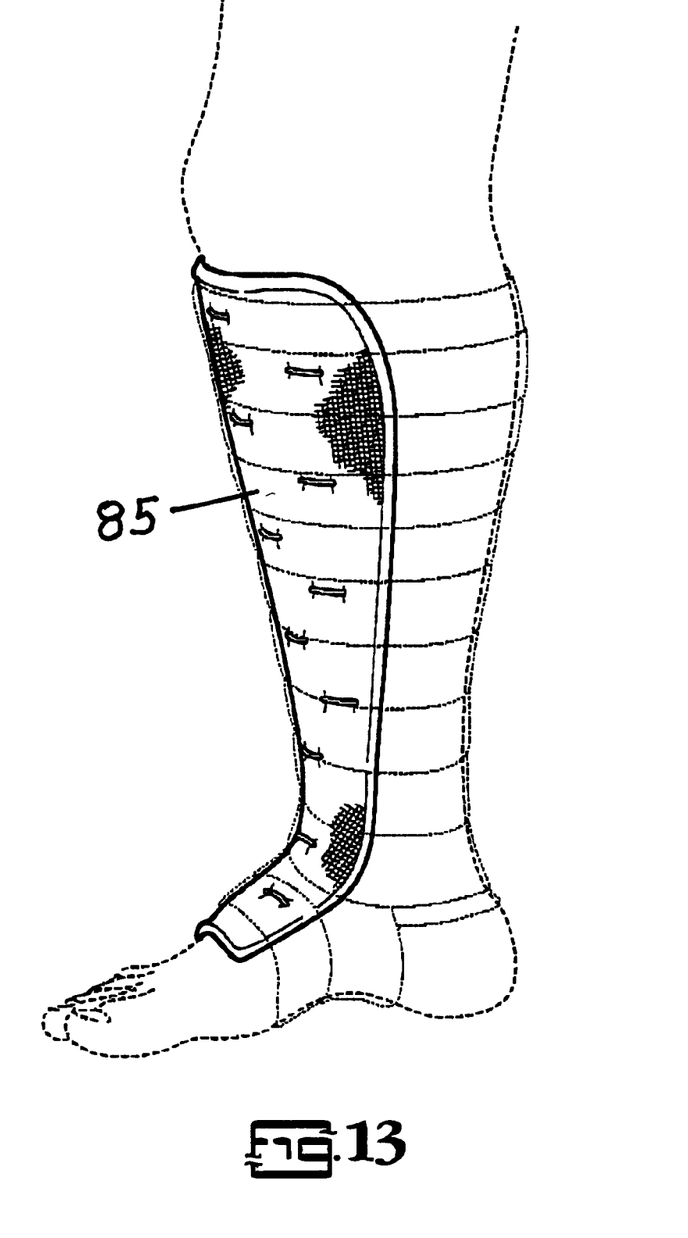
FIG. 13 illustrates the use of an elongated pillow as a "shin guard."

A large pillow such as pillow 85 shown in FIG. 12 may be used to cover parts of several regions such as the foot and shin area as shown in FIG. 13.

As seen, the present invention provides a method of and device for compressive treatment of lymphedema and other types of edema. The device of the present invention comprises an enclosure containing a medically effective amount of buckwheat hulls to form a pillow wherein said pillow is adapted for a compressive application and is also adapted to promote effective heat transfer. The device of the present invention thus absorbs heat from a swollen body part to buckwheat hulls contained within the device of the present invention. The method of the present invention comprises compressively applying an effective treatment amount for plurality of buckwheat hulls contained within an elastic, breathable, fabric enclosure to reduce edema or related a swelling.

I claim:

1. A method for treating edema and other types of swelling in a human in need thereof, comprising:
    compressively applying to a human in need thereof an effective treatment amount of a plurality of buckwheat hulls contained within an elastic, breathable, fabric enclosure onto said human in need thereof to reduce edema or related swelling.

2. A method of treating edema to inhibit tissue injury accompanying inflammation or swelling, comprising:
    administering to an epidermal region, a medicinally effective amount of buckwheat hulls contained within an elastic, breathable, fabric enclosure, said buckwheat hulls being compressively applied to said epidermal region of a human or an animal in need thereof.

3. A Therapeutic compress pillow for the treatment of edema and other tissue swelling in mammals comprising:
    a flexible, breathable, fabric enclosure containing a medically effective amount of buckwheat hulls adapted for compressive application to an epidermal region to reduce swelling in a mammal in need of such treatment.

4. A therapeutic compress pillow according to claim 3 wherein said medically effective amount of said buckwheat hulls has a planar distribution of between 10 and 30 hulls per square centimeter of said surface area of said enclosure in contact with said epidermal region.

5. A therapeutic compress pillow according to claim 3 wherein said flexible, breathable fabric enclosure is adapted to hold said enclosed buckwheat hulls in contact with said epidermal region.

6. A therapeutic compress pillow according to claim 5 which is a glove.

7. A therapeutic compress pillow according to claim 6 wherein said compress pillow is an enclosure secured within a glove.

8. A therapeutic compress pillow according to claim 5 wherein said flexible, breathable, fabric enclosure comprises a garment or a portion thereof.

* * * * *